Sept. 25, 1956 C. D. CORLISS Plant Pat. 1,520
EUONYMUS FORTUNEI PLANT
Filed March 18, 1955
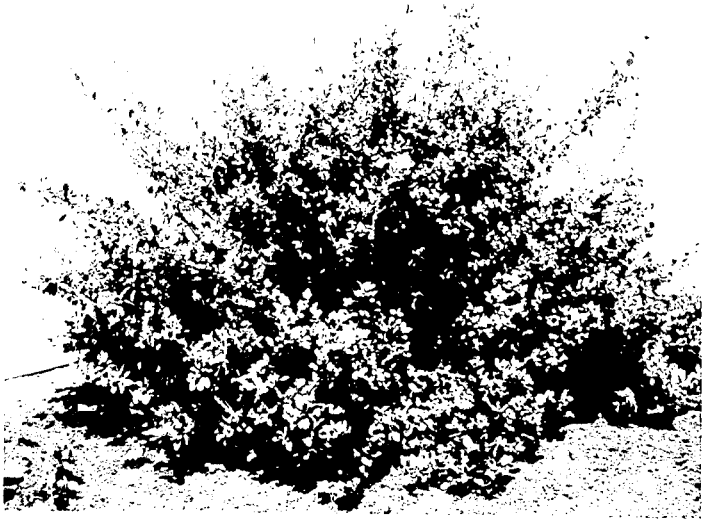
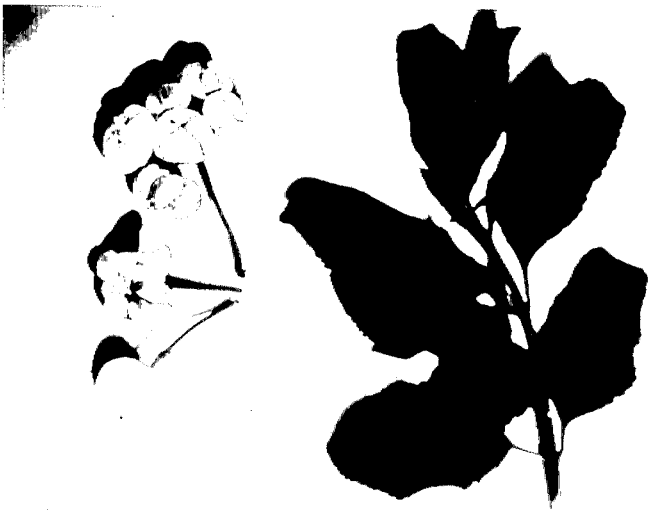
INVENTOR
Clifford D. Corliss
BY Orville M. Kile
PLANT PATENT AGENT United States Patent Office Plant Pat. 1,520
Patented Sept. 25, 1956

1,520

EUONYMUS FORTUNEI PLANT

Clifford D. Corliss, Gloucester, Mass., assignor to Corliss Bros., Inc., Gloucester, Mass., a corporation of Massachusetts Application March 18, 1955, Serial No. 495,366

1 Claim. (Cl. 47—59)

My present invention relates to a distinct variety of broadleaf evergreen Euonymus plant originating as the result of a cross made by me between *Euonymus fortunei vegeta* and *fortunei carrierei* (both unpatented) in an effort to obtain a sturdy, vigorous, upright broadleaf evergreen shrub of medium height and ornamental value. It is a striking variation from parental type, possessing definite decorative possibilities not found in either parent.

Asexual reproduction is the only means of obtaining plants of this variety. I have so reproduced it by cuttings, at our nurseries in Massachusetts and the new plants appear to exhibit the same characteristics as the original plant.

While both parent varieties of the original plant are essentially prostrate and usually able to assume a shrubby habit only by clinging to some support by means of aerial roots, my new variety is distinctly a shrub form and grows from a single central stem, without support and with greater compactness.

Outstanding features of the variety are its upright, robust, compact, wider-than-high, shrub growth and the generous supply of exceptionally large, brightly-colored fruits. In common with some others of my newer varieties of Euonymus, the plant of this variety produces an abundance of fibrous roots, thus permitting transplanting without difficulty. Also the variety is adaptable to various growing conditions, growing well in either semi-shade or full sun; in either moist or dry locations; and with no particular soil requirements. The variety appears to be resistant to drought and cold, as the original plant has been exposed to severe droughts and below-zero temperatures for a number of years, without any indication of injury or adverse effects, and later generations display the same resistant qualities.

The accompanying illustration is a black-and-white photographic portrayal of the original plant of this variety, with a cluster of leaves shown separately on the lower right and on the lower left an approximately accurate hand-colored cluster of the large berries of the variety.

In the following detailed description, color plate numbers refer to Ridgway's Color Standards and Nomenclature. Where no plate numbers are given, the usual dictionary meaning of the color terms is intended.

THE PLANT

Growth Habit: Upright, robust, compact shrub.

Form: Broader than high, with branches growing laterally from a central trunk to make a compact shrub well filled out at the base all the way to the ground.

Size: Plants of this variety have grown 5 to 6 feet tall and 8 to 10 feet across.

Roots: Numerous and fibrous, permitting easy digging and transplanting.

Drought tolerance: During the life of the original plant there has been no indication of injury from drought although exposed to severe drought conditions.

Hardiness: No indication of damage has been seen even at zero temperatures, although some other Euonymus varieties growing under the same conditions have at times shown die-back and stem injury. Has never shown any sign of winter burn although grown in real windswept plantings.

Branchlets: Minutely verrucose; light green; occasionally bearing adventitious roots.

Internodes: Length on main shoots 2½ to 5 cm.; shorter on side branches.

Leaf buds: Conical and long-pointed. Lateral buds ½ to 1 cm. long; terminal buds somewhat larger.

Bud scales: Imbricated; pale green.

Foliage:

*Type.*—Broadleaved; petioled; evergreen.

*Quantity.*—Abundant.

*Position.*—Opposite.

*Texture.*—Leathery, firm and tough.

*Size.*—Variable and in two types. Older leaves appearing on the short side branches toward the inside of the plant measure 5 to 7 cm. long and 3 to 3½ cm. broad. Large leaves on the new, vigorous growth measure 6½ to 8 cm. long and 3½ to 3 cm. wide.

*Shape.*—Ovate to broad-ovate. Apex slightly notched, turning downward on many of the leaves. On newer growth, apex acute; base acute; margin finely crenate. On older growth, apex obtuse; base obtuse; margin crenate-dentate. Revolute, with sides of leaf slightly turned downward.

*Color.*—Upper surface dark glossy green, between Hellebore and Forest Green (both Plate XVII), with veins of slightly lighter color. Under surface dull light green, approximately Courge Green (Plate XVII).

*Petioles.*—Strong; 1 to 1½ cm. long.

THE FLOWER AND FRUIT

Flower:

*Borne.*—In axillary cymes.

*Type.*—Inconspicuous.

*Size.*—Very small.

*Color.*—Greenish-white.

Fruit:

*Quantity.*—This variety fruits very heavily, producing a profusion of extraordinarily large capsules.

*Capsule.*—Buff to pink, with reddish-purple tinge. Sub-globose; lobed; slightly warty. Splits open at maturity to expose hanging, attractive orange seeds.

*Seed.*—Normally four in each capsule, each seed covered with a glistening, bright orange aril. Much larger than seed of other similar types of Euonymus plants.

Having thus disclosed my invention, I claim:

The new and distinct variety of broadleaf evergreen Euonymus plant, substantially as herein shown and described, characterized particularly by its broad, compact, upright, shrub growth from a single large main stem; its strong fibrous root system; its adaptability to various weather and soil conditions without apparent injury; its two leaf types on different parts of the plant; and its very generous supply of clusters of exceptionally large, colorful fruit capsules, with seeds much larger than those of other similar Euonymus varieties.

No references cited.